(12) United States Patent
D'Aquanni et al.

(10) Patent No.: US 7,662,132 B2
(45) Date of Patent: Feb. 16, 2010

(54) EXPANDABLE MEMBER FOR VENOUS LEAD FIXATION

(75) Inventors: Peter J. D'Aquanni, Murrieta, CA (US); Eric T. Johnson, Temecula, CA (US); Gayla A. Smith, Sun City, CA (US); Bruce A. Tockman, Scandia, MN (US); Brian D. Soltis, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 198 days.

(21) Appl. No.: 11/627,194

(22) Filed: Jan. 25, 2007

(65) Prior Publication Data

US 2008/0183267 A1 Jul. 31, 2008

(51) Int. Cl.
*A61N 1/00* (2006.01)

(52) U.S. Cl. ..................................... 604/116

(58) Field of Classification Search ............. 600/16–18, 600/508–528; 607/1–76, 115–156
See application file for complete search history.

(56) References Cited

U.S. PATENT DOCUMENTS

| | | | |
|---|---|---|---|
| 4,317,459 A | 3/1982 | Gilman | |
| 5,603,694 A * | 2/1997 | Brown et al. | 604/500 |
| 6,136,021 A | 10/2000 | Tockman et al. | |
| 6,161,029 A | 12/2000 | Spreigl et al. | |
| 6,711,443 B2 | 3/2004 | Osypka | |
| 6,741,893 B2 | 5/2004 | Smits | |
| 6,909,920 B2 | 6/2005 | Lokhoff et al. | |
| 6,968,237 B2 | 11/2005 | Doan et al. | |
| 7,139,614 B2 * | 11/2006 | Scheiner et al. | 607/125 |
| 2002/0161423 A1 | 10/2002 | Lokhoff et al. | |
| 2003/0220676 A1 | 11/2003 | Helland | |
| 2004/0059404 A1 | 3/2004 | Bjorklund et al. | |
| 2004/0243210 A1 | 12/2004 | Morgan et al. | |
| 2005/0070981 A1 | 3/2005 | Verma | |
| 2005/0080472 A1 | 4/2005 | Atkinson et al. | |
| 2006/0095078 A1 | 5/2006 | Tronnes | |
| 2008/0147160 A1 * | 6/2008 | Ghione et al. | 623/1.11 |

FOREIGN PATENT DOCUMENTS

| | | |
|---|---|---|
| WO | 2004028618 A1 | 4/2004 |
| WO | 2006132702 | 12/2006 |

OTHER PUBLICATIONS

International Search Report and Written Opinion of international application No. PCT/US2008/051695, mailed Jun. 5, 2008, 12 pp.

* cited by examiner

*Primary Examiner*—George Manuel
*Assistant Examiner*—Robert N Wieland
(74) *Attorney, Agent, or Firm*—Faegre & Benson LLP

(57) ABSTRACT

The present invention is directed to a cardiac lead for delivery to the left side of a patient's heart including a self-expanding fixation method positioned over the distal portion of the lead. The self-expanding fixation member is capable of automatically expanding from a collapsed state to an expanded state upon deployment at a target site in a cardiac vessel. The fixation member is configured such that in the expanded state it is biased to a side of the lead body.

19 Claims, 11 Drawing Sheets

EXPANDABLE MEMBER FOR VENOUS LEAD FIXATION

TECHNICAL FIELD

This invention is related to devices and methods for fixation of cardiac leads. Specifically, the present invention is directed to deployable devices and methods for acute and chronic fixation of a portion of a cardiac lead within a patient's coronary vasculature.

BACKGROUND

Implantable medical devices for treating irregular contractions of the heart with electrical stimuli are well known. Exemplary implantable devices are defibrillators and pacemakers. Various types of electrical leads for defibrillators and pacemakers have been suggested, many of which are placed transvenously. Such leads are introduced into the patient's vasculature at a venous access site and travel through veins to the sites where the leads' electrodes will be implanted or otherwise contact target coronary tissue. Electrodes for transvenously-placed leads can be implanted in the endocardium (the tissue lining the inside of the heart) of the right atrium or ventricle, or alternatively, in the branch vessels of the coronary venous system. In particular, lead electrodes can be implanted in the coronary sinus or a branch vessel thereof for sensing and/or stimulation of the left side of the heart (i.e., the left ventricle).

One difficulty with implanting leads in or about the heart is that the lead may become dislodged from its desired location during or after lead implantation. For example, the lead may become dislodged or otherwise repositioned when a clinician withdraws the guiding catheter used to initially implant the lead. Cardiac leads may also become dislodged by normal physiological activity. In an attempt to prevent cardiac leads from being dislodged, a variety of screws, anchors and other devices have been used to affix cardiac leads at a desired location at or near a patient's heart. Some of these devices, however, do not adequately affix the lead at the desired location. Other devices require a clinician to carry out complex, time-consuming steps during or after lead implantation to properly affix the lead at the desired location.

Thus, there is a need in the art for a device and method for fixating cardiac leads within the coronary vasculature which does not interfere with delivery of the lead and which can be deployed after delivery to provide acute and/or chronic fixation.

SUMMARY

According to one embodiment of the present invention, a cardiac lead includes a conductive lead body including at least one electrode and a preformed, self-expanding fixation member positioned over a distal portion of the lead body. The fixation member includes a distal end fixed to the lead body and a proximal end slideably adjacent to the lead body. The fixation member is configured such that when it is in an expanded state it is biased to a side of the lead body.

In another embodiment of the present invention, a cardiac rhythm management system includes a pulse generator, a conductive lead body coupled to the pulse generator, at least one electrode, and a preformed, self-expanding fixation member positioned over a distal portion of the lead body. The fixation member includes a distal end fixed to a distal end of the lead body and a proximal end slideably adjacent to the lead body. The fixation member is configured such that in an expanded state, it is biased to a side of the lead body.

In another embodiment of the present invention, a lead for placement in a coronary vessel includes a conductive lead body including at least one electrode and a fixation means for securing a distal end of the lead body in the coronary vessel. The fixation means includes a distal end fixed to a distal end of the lead body and a proximal end slideably adjacent to the lead body.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
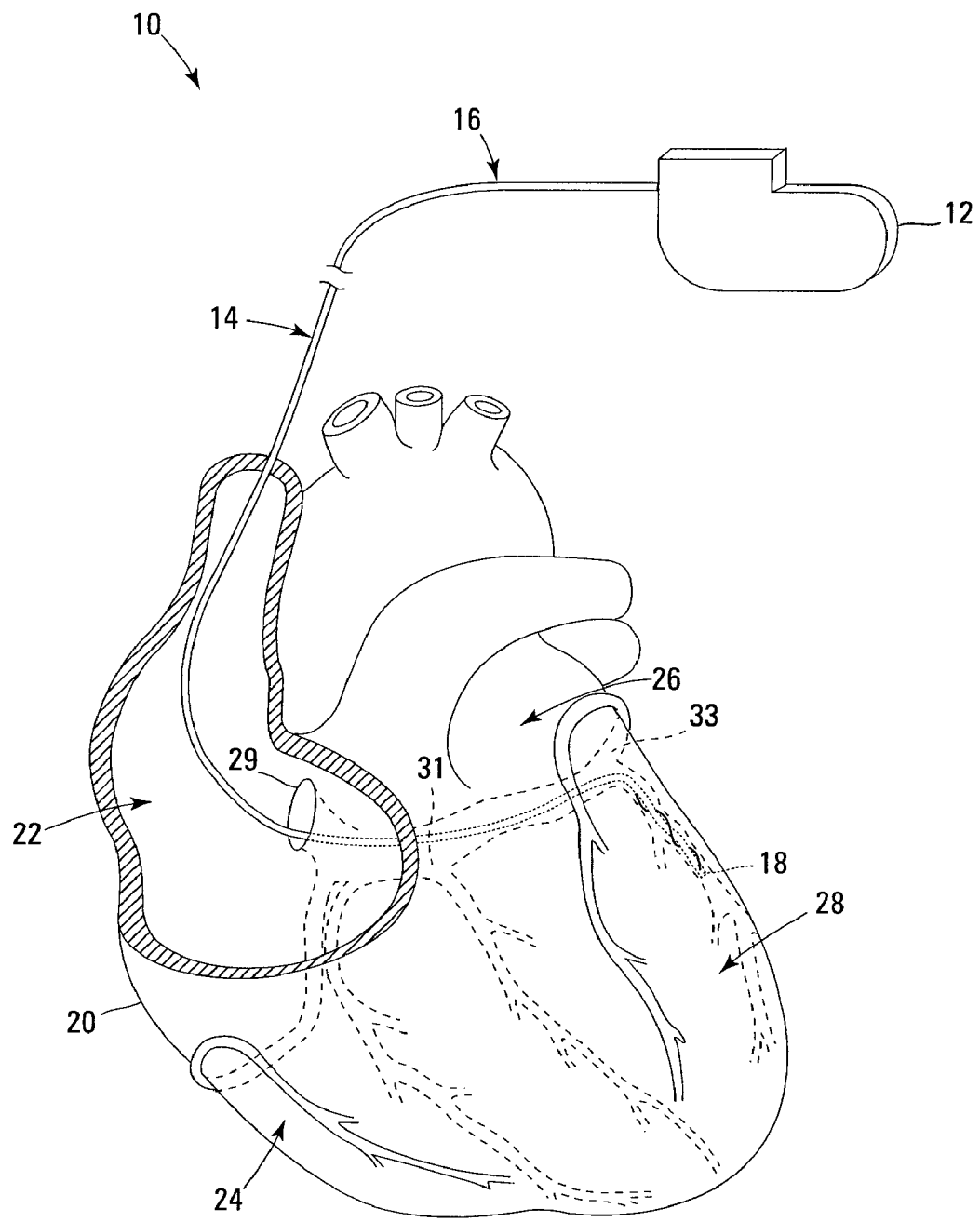
FIG. 1 is a schematic view of a cardiac lead implanted in a cardiac vessel.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management system 10 including a pulse generator 12 coupled to a lead 14 having a proximal end 16 and a distal end 18. As shown in FIG. 1, distal portions of the lead 14 are disposed in the patient's heart 20, which includes a right atrium 22, a right ventricle 24, a left atrium 26, and a left ventricle 28. In the embodiment illustrated in FIG. 1, the distal end 18 of the lead 14 is transvenously guided through the right atrium 22, through the coronary sinus ostium 29, and into a branch of the coronary sinus 31 or great cardiac vein 33. The illustrated position of the lead 14 can be used for sensing or for delivering pacing and/or defibrillation energy to the left side of the heart 20, or to treat arrhythmias or other cardiac disorders requiring therapy delivered to the left side of the heart 20.

Additionally, it will be appreciated that the lead 14 can also be used to provide treatment in other regions of the heart 20 (e.g., the right ventricle).

Figure 2A:
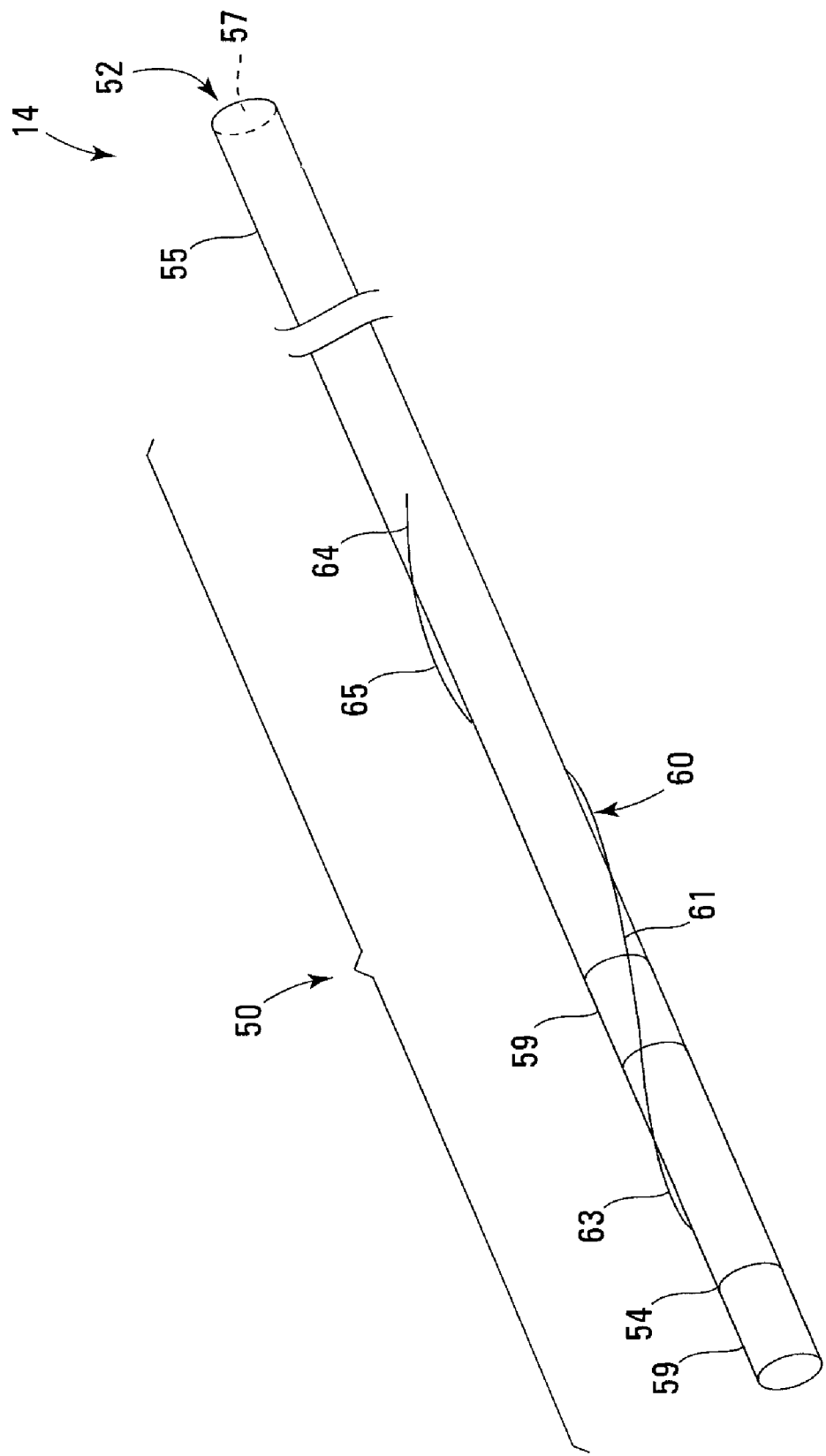
FIGS. 2A-2B show a side plan view of a distal portion of a cardiac lead according to one embodiment of the present invention.
Figure 2B:
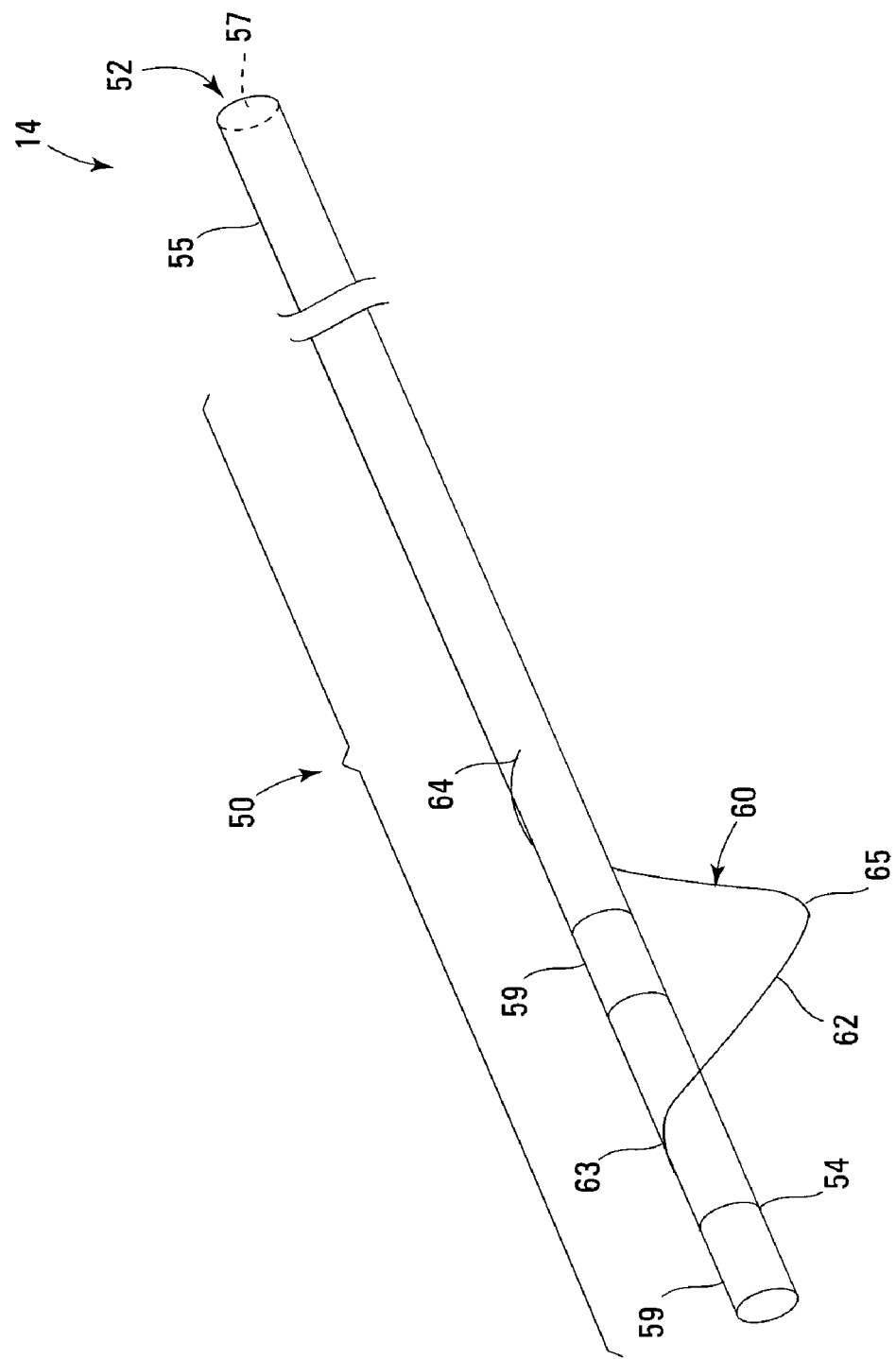

FIGS. 2A and 2B show schematic illustrations of a distal portion 50 of a cardiac lead 14 according to one embodiment of the present invention. As shown, the cardiac lead 14 includes a proximal end 52, a distal end 54, and a lead body 55 defining a lead lumen 57 extending between the proximal and distal ends 52, 54. In one embodiment of the present invention, the distal portion 50 includes approximately the distal 5-10 cm of the lead body 55. Additionally, the distal portion 50 of the cardiac lead 14 includes one or more electrodes 59 that are in electrical communication with a conductive element (not shown) extending through the lead lumen 57.

As shown in FIG. 2A, the distal portion 50 of the cardiac lead 14 includes a preformed, self-expanding fixation member 60. In FIG. 2A, the self-expanding fixation member 60 is shown in a collapsed configuration 61. In FIG. 2B the fixation member 60 is shown in an expanded configuration 62. In one embodiment of the present invention, the cardiac lead 14 is configured such that conventional lead implantation procedures can be utilized while still allowing for the actuation of the self-expanding fixation member 60. More particularly, the lead body 55 can be configured to allow for the passage of a guiding member such as a guide wire or stylet through the lead lumen, without interfering with the deployment and/or retraction of the self-expanding fixation member 60.

Figure 3:
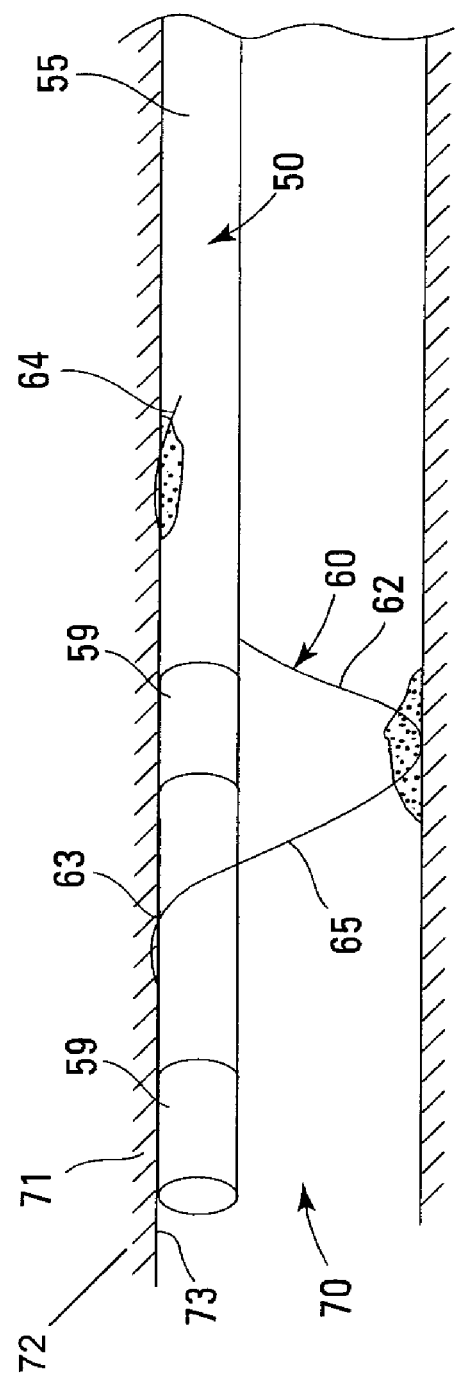
FIG. 3 shows a sectional view of the distal portion of the lead shown in FIGS. 2A-2B deployed in a cardiac vessel according to an embodiment of the present invention.

The self-expanding fixation member 60 is a pre-formed spiral, helical, or corkscrew-shaped wire or coil that is capable of automatically expanding from a collapsed configuration 61 (illustrated in FIG. 2A) to a pre-formed expanded configuration 62 (illustrated in FIG. 2B) when deployed at a target site in a coronary vessel (shown in FIG. 3). According to one embodiment of the invention, the wire or coil forming the preformed, self-expanding fixation member 60 has an effective outer diameter ranging from about 0.005 to about 0.007 inches. The self-expanding fixation member 60 includes a distal end 63, a proximal end 64 and a body 65. The distal end 63 of the self-expanding fixation member 60 is secured to the distal portion 50 of the lead body 55 using an appropriate measure such as an adhesive. Other means of securing the distal end 63 of the self-expanding fixation member 60 may be readily apparent to those of skill in the art.

In contrast to the fixed distal end 63 of the fixation member 60, the proximal end 64 is slideably adjacent to the lead body 55. Specifically, the proximal end 64 is not attached to the lead body 55 and is capable of sliding in a distal direction during expansion and in a proximal direction during collapse. The self-expanding fixation member 60 is positioned over the distal portion 50 of the lead body 55 adjacent or in proximity to the lead's electrode(s) 59.

According to a further embodiment of the present invention, the proximal end 64 includes a protective feature such as a polymer cover or end cap. In this embodiment, the protective feature protects the vessel wall from potential damage during deployment of the fixation member 60 in the vessel. The protective feature is removable such that the helix 60 can be released and extracted through any fibrosis that is formed around it. According to another exemplary embodiment, the protective feature is a bio-absorbable polymer (e.g. mannitol) that dissolves over an extended period of time.

As illustrated in FIG. 3, the lead body 55 is inserted into a vessel lumen 70. In an expanded configuration 62, the self-expanding fixation member 60 is biased to one side of the lead body 55. This allows the lead body 55 to be pushed to one wall 71 of the coronary vessel 72 in which it is deployed, improving electrode contact with the vessel wall 71. The fixation member 60 provides a significant amount of force to the vessel wall 71, but allows for adjustment and repositioning of the distal portion 50 of the lead body 55 in the coronary vessel 72. According to one embodiment of the present invention, the fixation member 60 has a shape, diameter, elasticity and structure to provide a sufficient frictional force to the vessel wall 71 such that when expanded, the fixation member 60 is capable of securing and stabilizing the distal portion 50 in the coronary vessel 72. When a proximal removal force is applied to the lead body 55 tension is applied to the distal end of the fixation member 60. Tension applied to the distal end of the expanded fixation member 60 causes the fixation member 60 initially to further expand, applying additional frictional force to the vessel wall 71.

The fixation member 60 expands to a size determined by the inner diameter 73 of the vessel lumen 70. In one embodiment according to the present invention, the self-expanding fixation member 60 expands to an effective diameter that is slightly larger than the anticipated anatomical diameter of the vessel in which it is deployed. According to one embodiment of the present invention, an effective diameter of the self-expanding fixation member 60 ranges from about 4 to about 8 millimeters. Once positioned in a vessel lumen 70, the self-expanding fixation member 60 can deform or flatten as it applies force to the vessel wall 71.

The preformed, self-expanding fixation member 60 can be formed from a variety of super-elastic or self-expanding materials having any suitable cross-sectional shape as is known in the art. According to one embodiment of the present invention, the selected materials are shape memory materials and have sufficient elasticity to expand upon deployment at a target site in a coronary vessel. Such self-expanding materials are well known in the art. In one embodiment, the self-expanding fixation member 60 is made from a nickel-titanium alloy such as Nitinol. In other embodiments according to the present invention, the self-expanding fixation member 60 can be made from other materials including, but not limited to, the following: bio-compatible polymers, bio-resorbable polymers, polyurethane, titanium, spring temper 316 SS, MP35N, platinum or platinum alloys, and combinations thereof. Other materials well known in the art can also be used for forming the self-expanding fixation member 60. The material or combination of materials should be selected such that it has a high elasticity range allowing the self-expanding fixation member 60 to expand and collapse without deformation. In one embodiment of the present invention, the Young's Modulus ranges from about 12 Msi to about 29 Msi.

According to one embodiment of the present invention, a conductive material is selected for the fixation member 60. In this embodiment, the cardiac lead 14 is configured such that the fixation member 60 is in electrical communication with a conductive element. This configuration allows the fixation member 60 to be used as an electrode. Due to the biased configuration of the fixation member 60, electrical contact with a vessel wall 71 is ensured.

According to a further embodiment of the present invention, the fixation member 60 can comprise or, alternatively, be coated with a radiopaque substance such that standard visualization techniques can be used to visualize the fixation member 60 during insertion and/or removal. Alternatively, the distal portion 50 of the lead body 55 can include a radiopaque marker to assist in visualization.

Figure 4A:
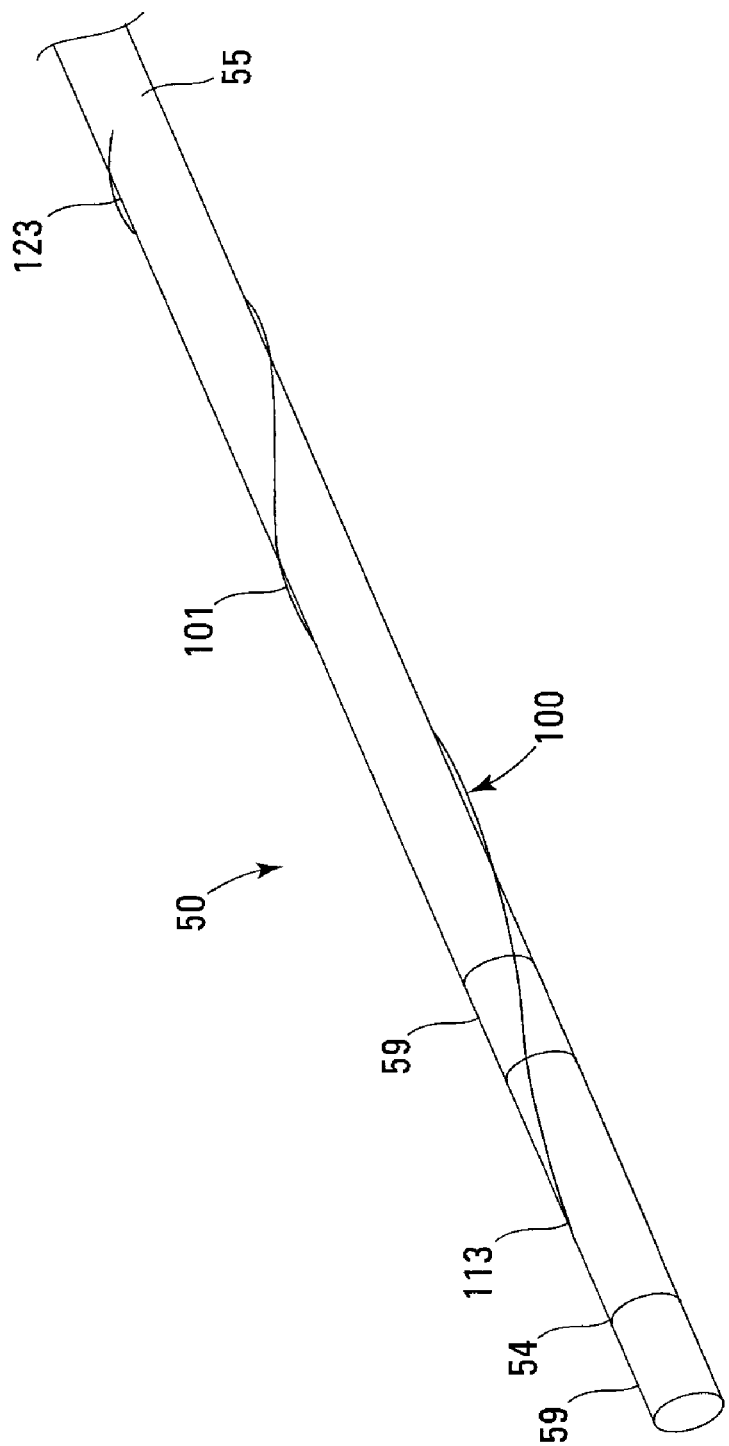
FIGS. 4A-4B show a side plan view of a distal portion of a cardiac lead according to another embodiment of the present invention.
Figure 4B:
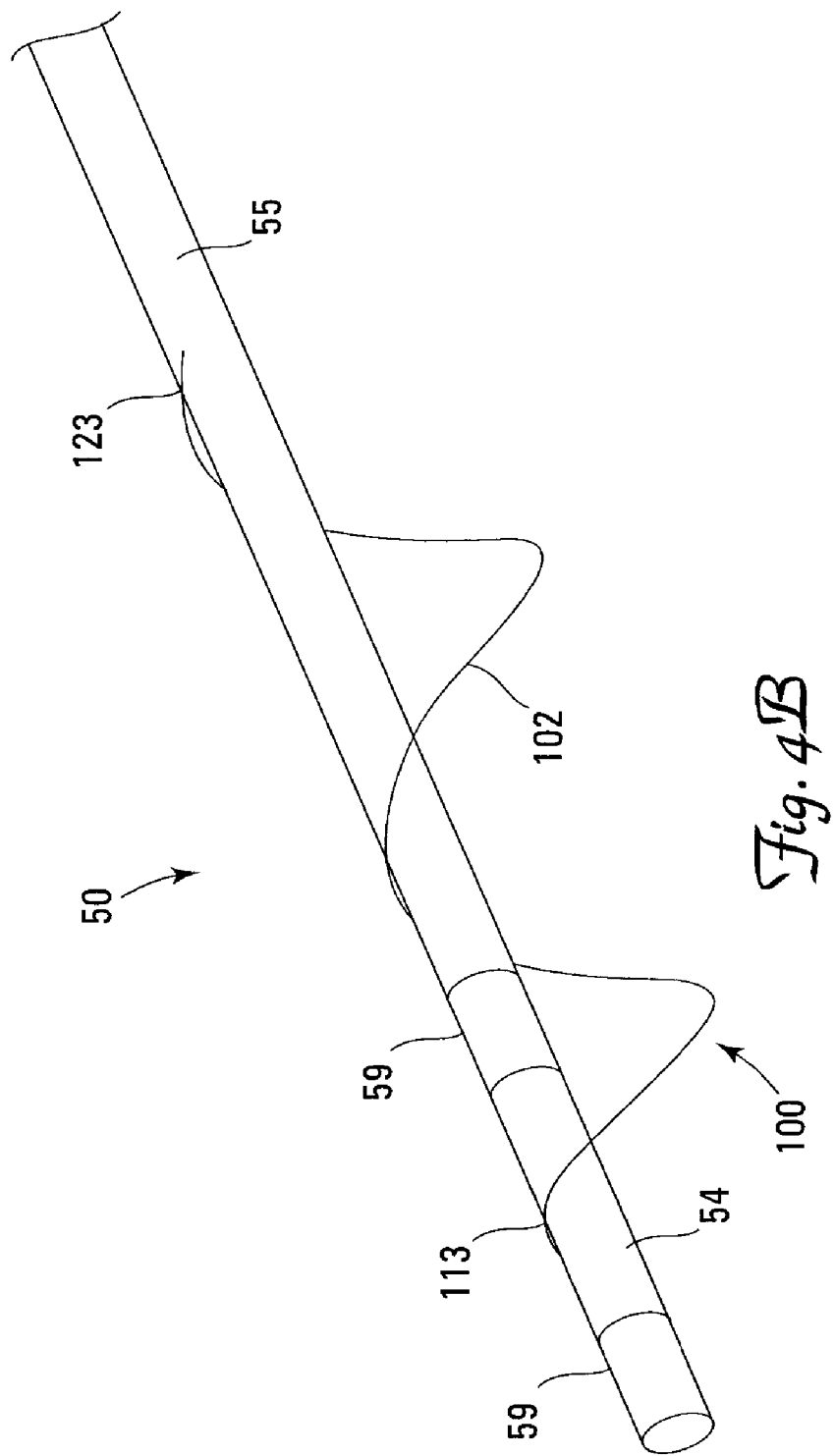

FIGS. 2B and 4B show the preformed, self-expanding fixation member 60, 100 in an expanded configuration. In the expanded configuration, according to one exemplary embodiment of the present invention, the length of the self-expanding fixation member 60, 100 ranges from about 0.5 to about 1.5 inches along the distal portion 50 of the lead body 55. Over its expanded length, the self-expanding fixation member 60, 100 can have one to four peaks. In one exemplary embodiment of the present invention, shown in FIG. 2B, the preformed, self-expanding fixation member 60 includes a single peak when in the expanded configuration. In another exemplary embodiment, shown in FIG. 4B, the self-expanding fixation member 100 has more than one peak. Additional peaks may be appropriate as determined by those of skill in the art. In the embodiment shown in FIG. 4B, the peaks occur at regular intervals and are spaced further apart from one another than is typically found in a typical helix fixation member. According to a further embodiment of the present invention, the self-expanding fixation member 60 is a preformed, elongated spiral.

According to another embodiment of the present invention, as shown in FIGS. 4A-4B, the preformed, self-expanding fixation member 100 is a helical, spiral, or corkscrew-shaped wire including two peaks. FIG. 4A shows the fixation member 100 in a collapsed configuration 101. FIG. 4B shows the fixation member 100 in an expanded configuration 102. Like the fixation member illustrated in FIGS. 2A-2B, the fixation member 100 is positioned over the distal portion 50 of a lead body 55 adjacent or in proximity to the lead's electrode(s) 59. The fixation member 100 includes a distal end 113 secured to a distal end 54 of the lead body 55. The distal end 113 of the self-expanding fixation member 100 is secured to the lead body 55 using an appropriate measure such as adhesive. Other means of securing the distal end 113 of the fixation member 100 may be readily apparent to those of skill in the art. In contrast to the fixed distal end 113 of the self-expanding fixation member 100, the proximal end 123 is slideably adjacent to the lead body 55. Specifically, the proximal end 123 is not attached to the lead body 55 and capable of sliding in a distal direction during expansion and in a proximal direction during collapse.

Figure 5A:
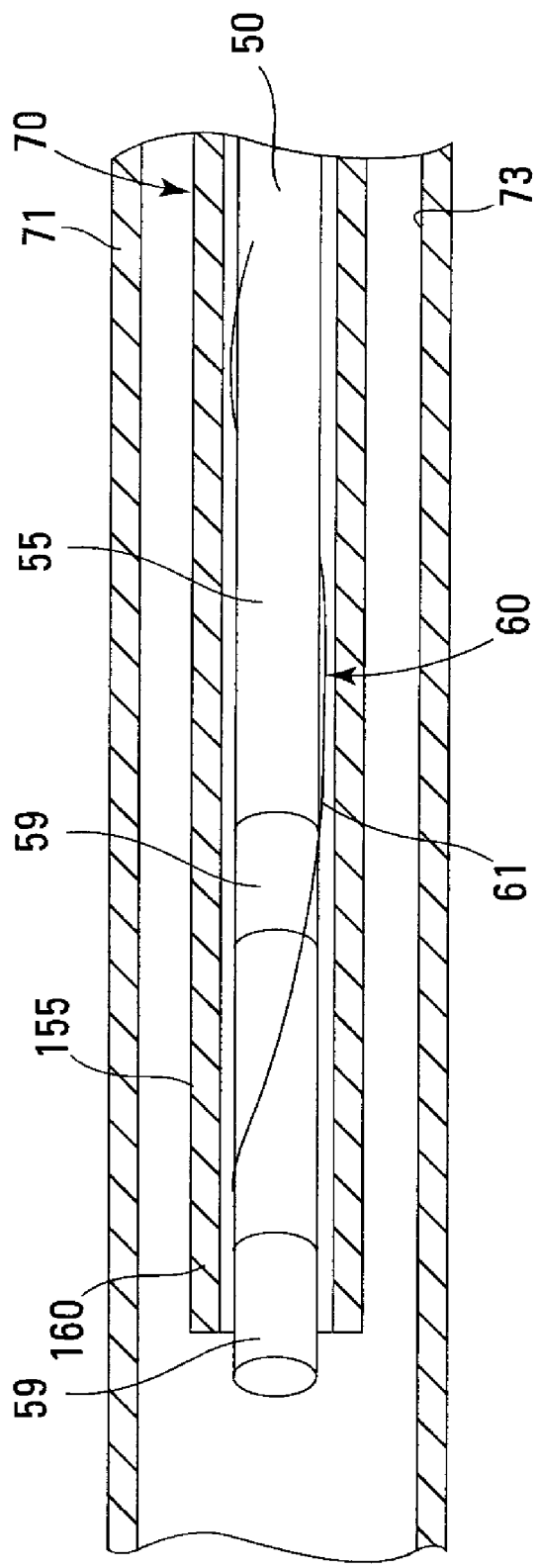
FIGS. 5A-5B show a partial sectional view of a distal portion of a cardiac lead as shown in FIGS. 2A-2B during implantation in a vessel using a delivery catheter.
Figure 5B:
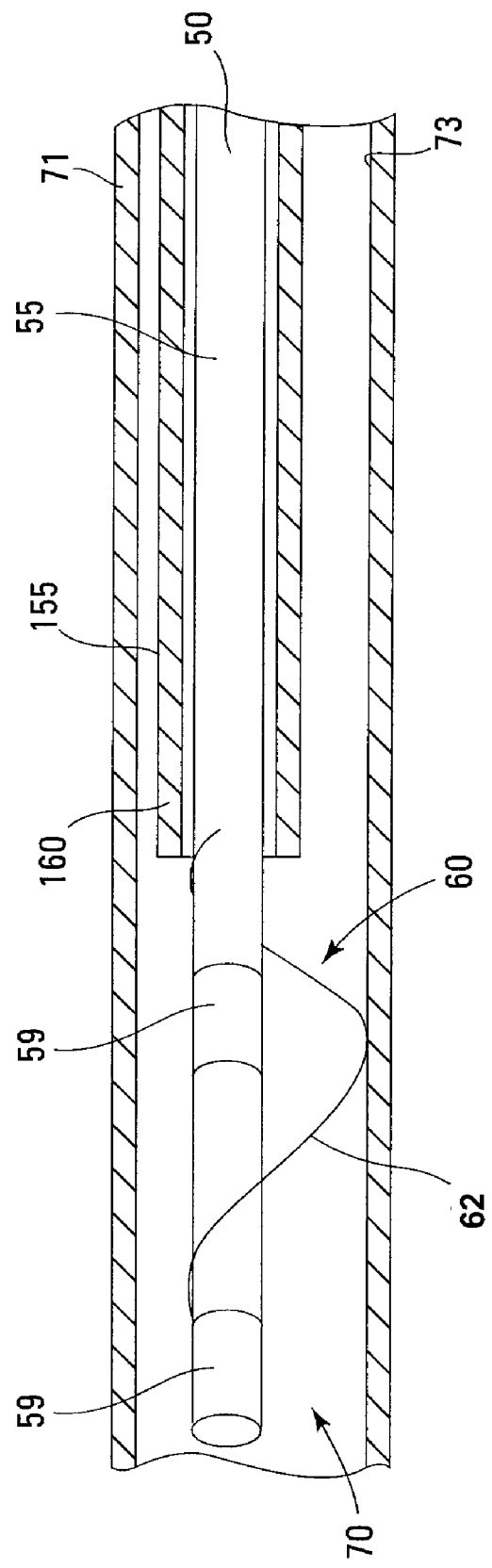

FIGS. 5A-5B show a distal portion 50 of a cardiac lead 14 as shown in FIGS. 2A-2B during delivery and implantation in a vessel lumen 70. As shown in FIG. 5A, a distal portion 50 of a cardiac lead body 55 is inserted into a delivery sheath 155 collapsing the self-expanding fixation member 60 to its collapsed configuration 61. Once the distal portion 50 of the lead body 55 has reached a target site in a coronary vessel, the distal portion 50 of the lead body 55 is exposed allowing the self-fixation member 60 to expand to its expanded configuration 62, shown in FIG. 5B. As illustrated in FIG. 5B, in its expanded configuration 62, the self-expanding fixation member 60 is biased to one side of the lead body 55.

In one embodiment of the present invention, the delivery sheath 155 is proximally withdrawn over the distal portion 50 of the lead 14, exposing the distal portion 50 of the lead body 55. In another embodiment according to the present invention, the distal portion 50 of the lead body 55 is pushed distally beyond a distal end 160 of the delivery sheath 155 such that the distal portion 50 is exposed and the fixation member 60 is released from its collapsed state 61 automatically expanding to its expanded state 62. Additionally, according to one embodiment of the present invention, the delivery sheath 155 is completely removed from a vessel lumen 70. Alternatively, once the distal portion 50 of the lead body 55 has been exposed, the delivery sheath 155 remains in the vessel lumen 70.

The delivery sheath 155 can be made from a variety of biocompatible materials having sufficient strength to retain the self-expanding fixation member in a collapsed configuration. For example, the sheath 155 can be formed from a variety of suitable biocompatible polymeric materials such as medical grade silicone or polyurethane.

Figure 6:
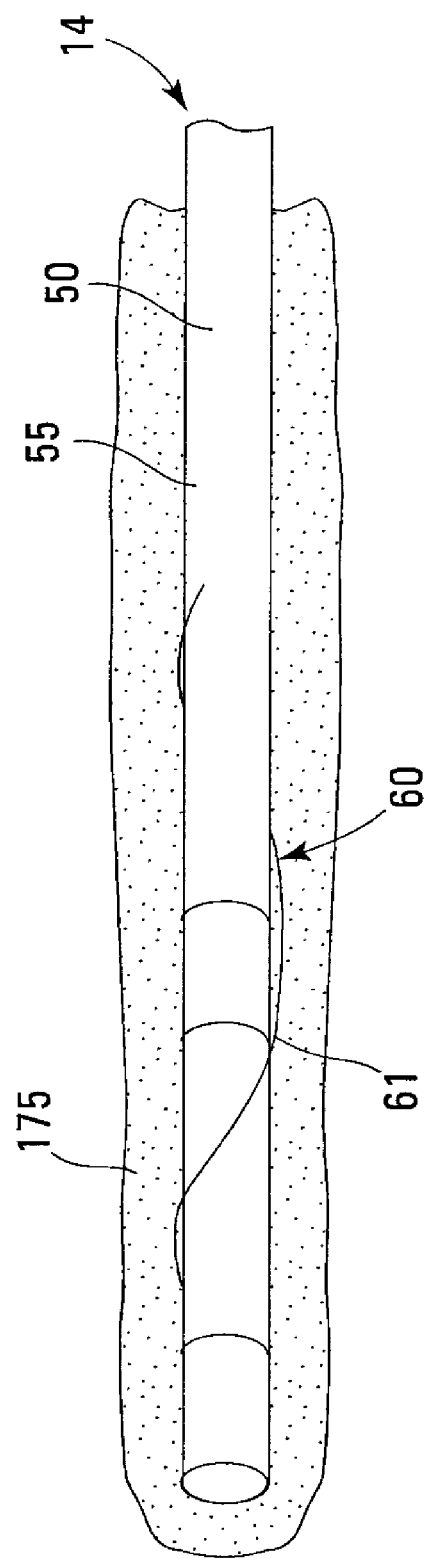
FIG. 6 shows a sectional view of a distal portion of a lead according to an embodiment of the invention including a bio-absorbable tip.

In an alternate embodiment of the present invention, as shown in FIG. 6, the cardiac lead 14 includes a bio-absorbable material 175 coating the distal portion 50 of the lead 14 including the self-expanding fixation member 60. The bio-absorbable coating 175 is capable of retaining the self-expanding fixation member 60 in the collapsed state 61 during delivery of the distal portion 50 to a target site in a cardiac vessel. According to this embodiment, a guide catheter or a delivery sheath is used to deliver the distal portion 50 of the lead 14. When the guide catheter or delivery sheath is removed, the distal portion 50 including the bio-absorbable coating 175 is exposed. The bio-absorbable coating 175 is readily absorbed into the blood stream allowing the self-expanding fixation member 60 to automatically expand to its predetermined, expanded state. An example of a bio-absorbable material used to coat the distal portion 50 is a sugar such as mannitol. Other sugars and bio-absorbable materials known in the art may be used to coat the distal portion 50.

Figure 7:
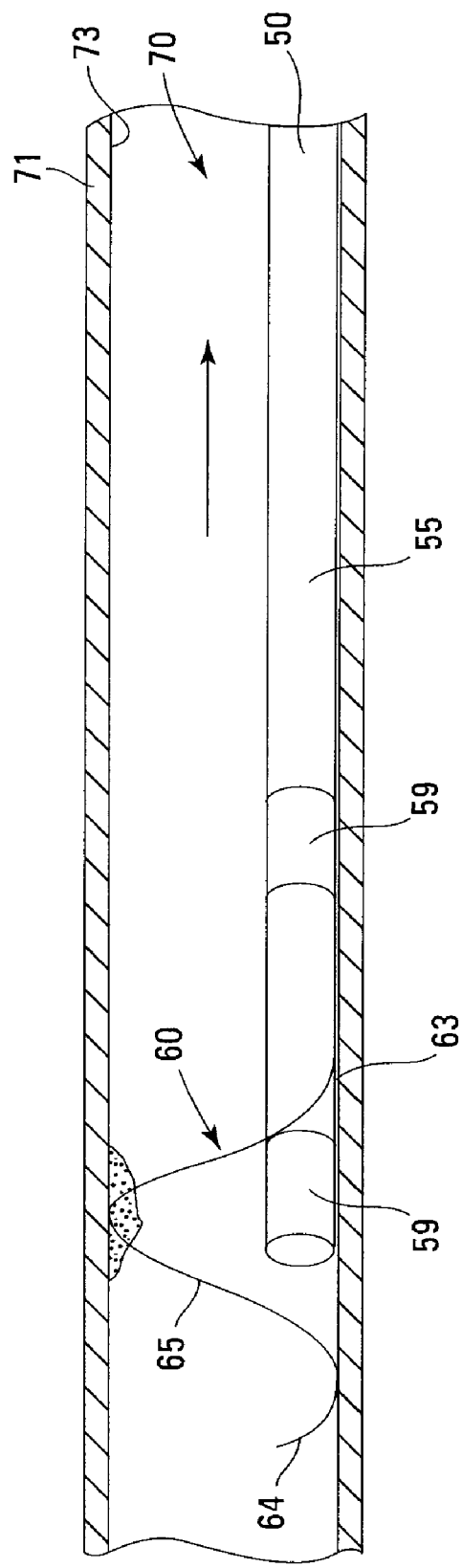
FIG. 7 shows a side plan view of an embodiment of the present invention during and/or after removal of the cardiac lead.

The self-expanding fixation member 60, according to the embodiments of the present invention, allows a distal portion 50 of a cardiac lead body 55 to be repositioned and/or removed after acute or chronic fixation has occurred. This is due in part to the configuration of the fixation member 60 having its proximal end 64 not attached to the lead body 55. Additionally, the wire comprising the fixation member 60 has no structural elements such as meshing, pores, threads, tines, allowing for tissue in-growth. Fibrosis may occur around the wire comprising the fixation member 60. During repositioning or removal, the lead is first moved in a distal direction to free the proximal end 64 of the fixation member 60 from any fibrosis surrounding it. Then, the distal portion 50 of the lead is moved to a position proximal to the target location. As the distal portion 50 of the lead continues to move in a proximal direction, indicated by the directional arrow in FIG. 7, the fixation member 60 becomes prolapsed such that the proximal end 64 of the fixation member 60 is located distal to and trails the fixed distal end 63. The prolapsed fixation member 60 then follows a path formed in the fibrosis by the initial deployment of the fixation member 60. The distal portion 50 of the lead can then either be repositioned or removed.

Figure 8:
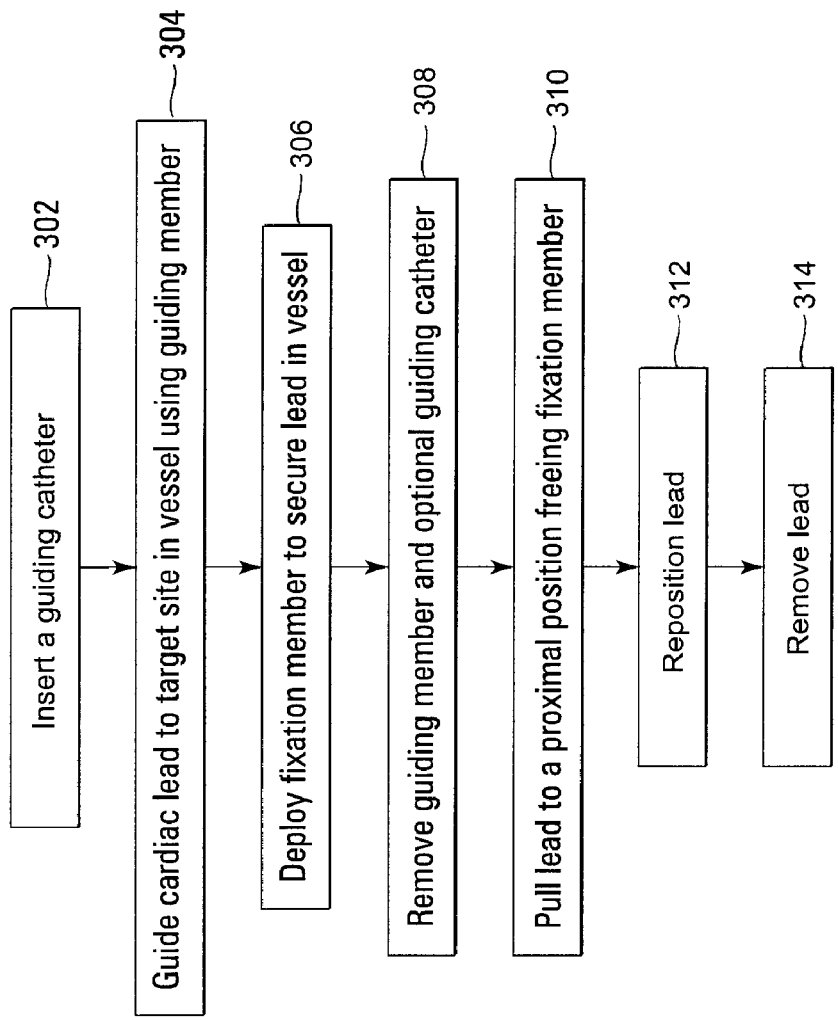
FIG. 8 is a block diagram illustrating a method of delivering and securing a cardiac lead according to the present invention.

FIG. 8 shows a method of implanting the cardiac lead 14 according to an embodiment of the present invention. Initially, one or more delivery sheaths or guiding catheters can be guided into a desired vessel (block 302). The cardiac lead, which is configured such that the fixation member is in the collapsed configuration, can then be guided through the delivery sheath or guiding catheter(s) to a target site in a cardiac vessel using a guiding member such as a guide wire or a stylet (block 304). After positioning the distal end of the lead at the target site, the fixation member can then be deployed into its expanded configuration to contact an inner surface of the patient's vessel lumen and to secure the distal end of the cardiac lead at the desired site (block 306). After fixation, the delivery sheath and guide member can be removed without dislodging the distal end of the lead device (block 308). The fixation member is capable of substantially permanent deployment to prevent the lead device from becoming dislodged or otherwise repositioned upon removal of the delivery sheath or as a result of normal physiological activity. The fixation member can be used for acute fixation or chronic fixation of a cardiac lead. The fixation member can be repositioned or removed as desired after acute or even chronic fixation. In order to free the fixation member, the lead is pulled to a proximal position (block 310). Once the fixation member has been freed, the lead can be either repositioned or removed (block 312, 314).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A cardiac lead comprising:
   a lead body having an outer surface and including a proximal end adapted to be connected to a pulse generator, a distal end, and a lumen adapted to receive a guiding member extending between the proximal end and the distal end;
   at least one conductor extending within the lead body from the proximal end to the distal end;
   at least one electrode located on the lead body operatively coupled to the at least one conductor;
   a preformed, self-expanding helical fixation member positioned externally over a distal portion of the lead body adjacent to the at least one electrode, the fixation member including a distal end fixed to the outer surface of the lead body and an unattached, free proximal end slideably adjacent to the outer surface lead body such that the unattached free proximal end is adapted to slide along the outer surface of the lead body when the fixation member is transitioned from a collapsed configuration to an expanded configuration, wherein the fixation member is preformed such that in the expanded configuration the fixation member is biased to a side of the lead body.

2. The cardiac lead according to claim 1, wherein the self-expanding helical fixation member comprises a wire or coil extending over a length of the distal portion ranging from about 0.05 inches to about 1.5 inches in the expanded configuration.

3. The cardiac lead according to claim 1, wherein the self-expanding fixation member is in a collapsed configuration during insertion into a patient's vasculature.

4. The cardiac lead according to claim 1, wherein the fixation member comprises a material having a Young's Modulus ranging from about 12 to about 29 Msi.

5. The cardiac lead according to claim 1, wherein the fixation member is made from a material comprising Nitinol, nickel-titanium alloy, titanium, polyurethane, 316 SS, MP35N, platinum, platinum alloy, a biocompatible polymer, a bio-resorbable polymer, or combinations thereof.

6. The cardiac lead according to claim 1, wherein the fixation member comprises a wire or a coil having an outer diameter ranging from about 0.005 to about 0.007 inches.

7. The cardiac lead according to claim 1, wherein in the expanded configuration the self-expanding fixation member has an effective diameter ranging from about 4 to about 8 millimeters.

8. A cardiac rhythm management system for delivering therapy to a heart, the system comprising:
   a lead body having an outer surface including a proximal end adapted to be connected to a pulse generator, a distal end, and a lumen extending there between, the lead body being configured to allow passage of a guiding member through the lead lumen;
   at least one conductor extending within the lead body from the proximal end to the distal end;
   at least one electrode located on a distal portion of the lead body and operatively coupled to the at least one conductor;
   a pulse generator electrically coupled to the at least one conductor at the proximal end of the lead body;
   a pre-formed, self-expanding helical fixation member positioned externally over the distal portion of the lead body adjacent to the at least one electrode, the fixation member including a distal end fixed to the distal end of the lead body and an unattached, free proximal end slideably adjacent to the lead body such that the unattached, free proximal end is adapted to slide along the outer surface of the lead body when the fixation member is transitioned from a collapsed configuration to an expanded configuration, the fixation member being pre-formed such that in an expanded configuration the fixation member is biased to a side of the lead body; and
   a delivery sheath adapted to be retracted in a proximal direction to deploy the self-expanding fixation member at a target site in a coronary vessel.

9. The cardiac rhythm management system according to claim 8 further comprising a guiding member for guiding the lead through a patient's vasculature.

10. The cardiac rhythm management system according to claim 8, wherein the self-expanding helical fixation member comprises a wire or coil extending over a length of the distal portion ranging from about 0.05 inches to about 1.5 inches in the expanded configuration.

11. The cardiac rhythm management system according to claim 8, wherein the self-expanding fixation member comprises a wire or a coil having an outer diameter ranging from about 0.005 to about 0.007 inches.

12. The cardiac rhythm management system according to claim 8, wherein the self-expanding fixation member comprises a material having a Young's Modulus ranging from about 12 to about 29 Msi.

13. The cardiac rhythm management system according to claim 8, wherein in the expanded configuration, the self-expanding fixation member has an effective diameter ranging from about 4 to about 8 millimeters.

14. A lead for placement in a coronary vessel of a human heart, the lead comprising:
   a lead body having an outer surface and including a proximal end adapted to be coupled to a pulse generator, a distal end, and a lumen extending there between;
   at least one conductor extending within the lead body from the proximal end to the distal end;
   at least one electrode located on the lead body and operatively coupled to the at least one conductor; and
   a fixation means for securing the distal end of the lead body in the coronary vessel disposed externally over the outer surface of the lead body, the fixation means having a distal end fixed to the distal end of the lead body and an unattached, free proximal end slideably adjacent to the lead body such that the unattached, free proximal end is adapted to slide along the outer surface of the lead body when the fixation means is transitioned from a collapsed configuration to an expanded configuration.

15. The lead according to claim 14, wherein the fixation means comprises a spiral, helical, or corkscrew-shaped wire.

16. The lead according to claim 14, wherein when the fixation means expands from the collapsed configuration to the expanded configuration, the fixation means is biased to a side of the lead body.

17. The cardiac lead according to claim 14, wherein the fixation means comprises a material having a Young's Modulus ranging from about 12 to about 29 Msi.

18. The cardiac lead according to claim 14, wherein the fixation means comprises a wire or a coil having an outer diameter ranging from about 0.005 to about 0.007 inches.

19. The cardiac lead according to claim 14, wherein the fixation means has a preformed shape.

* * * * *

UNITED STATES PATENT AND TRADEMARK OFFICE
CERTIFICATE OF CORRECTION

PATENT NO. : 7,662,132 B2 Page 1 of 1
APPLICATION NO. : 11/627194
DATED : February 16, 2010
INVENTOR(S) : D'Aquanni et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 220 days.

Signed and Sealed this

Thirtieth Day of November, 2010

David J. Kappos
*Director of the United States Patent and Trademark Office*